(12) United States Patent
Lee

(10) Patent No.: US 9,629,449 B2
(45) Date of Patent: Apr. 25, 2017

(54) PORTABLE INTERDENTAL TOOTHBRUSH

(71) Applicant: Sang Geun Lee, Gwangju-si (KR)

(72) Inventor: Sang Geun Lee, Gwangju-si (KR)

( * ) Notice: Subject to any disclaimer, the term of this patent is extended or adjusted under 35 U.S.C. 154(b) by 0 days.

(21) Appl. No.: 14/906,147

(22) PCT Filed: Apr. 13, 2015

(86) PCT No.: PCT/KR2015/003664
§ 371 (c)(1),
(2) Date: Jan. 19, 2016

(87) PCT Pub. No.: WO2015/122754
PCT Pub. Date: Aug. 20, 2015

(65) Prior Publication Data
US 2016/0338481 A1  Nov. 24, 2016

(30) Foreign Application Priority Data

Feb. 12, 2014 (KR) .................. 10-2014-0016234
Feb. 13, 2014 (KR) .................. 10-2014-0016931

(51) Int. Cl.
*A46B 11/00* (2006.01)
*A61C 15/00* (2006.01)
*A46B 9/04* (2006.01)

(52) U.S. Cl.
CPC .............. *A46B 11/001* (2013.01); *A46B 9/04* (2013.01); *A46B 11/0041* (2013.01); *A46B 11/0055* (2013.01); *A61C 15/00* (2013.01); *A46B 2200/108* (2013.01)

(58) Field of Classification Search
CPC combination set(s) only.
See application file for complete search history.

(56) References Cited

U.S. PATENT DOCUMENTS

| 6,688,796 | B1 * | 2/2004 | Liu | A45D 34/042 |
| | | | | 401/172 |
| 8,021,068 | B2 * | 9/2011 | Shih | A45D 34/042 |
| | | | | 401/277 |
| 8,308,384 | B2 * | 11/2012 | Zhang | A45D 34/042 |
| | | | | 401/171 |
| 2013/0340185 | A1 | 12/2013 | Patel et al. | |

FOREIGN PATENT DOCUMENTS

| KR | 10-2004-0008970 | 1/2004 |
| KR | 10-2007-0074304 | 7/2007 |
| KR | 20-2012-0007150 | 10/2012 |
| KR | 20-0465554 | 2/2013 |

OTHER PUBLICATIONS

English Translation of 10-2004-0008970.
English Translation of 20-2012-0007150.
English Translation of 20-0465554.
English Translation of 10-2007-0074304.

* cited by examiner

*Primary Examiner* — David Walczak
(74) *Attorney, Agent, or Firm* — KORUS Patent, LLC; Seong Il Jeong

(57) ABSTRACT

A portable interdental toothbrush is provided that can be carried conveniently since a cleaning solution tube is present in a sealed state when carried without using it. The portable interdental toothbrush provides convenience in use, simple structure, easy manufacture, and low production cost, thereby allowing any user to use it, and promotes the dental and oral health for citizens.

3 Claims, 9 Drawing Sheets

PORTABLE INTERDENTAL TOOTHBRUSH

CROSS-REFERENCE TO RELATED APPLICATION(S)

This application claims the benefit of International Application No. PCT/KR2015/003664, filed on Apr. 13, 2015, based on Korean Patent Application No. 10-2014-0016234, filed on Feb. 12, 2014, and Korean Patent Application No. 10-2014-0016931, filed on Feb. 13, 2014, with the Korean Intellectual Property Office, the disclosures of which are herein incorporated by reference in their entireties.

BACKGROUND

1. Technical Field

The present invention relates to a portable interdental toothbrush and is more particularly concerned with a portable interdental toothbrush in which a user can carry for portable use during travel or outing so as to clean and sterilize foreign materials and plaque that fit between teeth after meals; a cleaning solution tube for easily supplying a cleaning solution to the toothbrush in a state of carrying the interdental toothbrush is detachably attached, the cleaning solution is supplied to the interdental toothbrush via the cleaning solution tube, it is possible to separate the cleaning solution tube, replenish the cleaning solution and attach it again; its use is convenient, the structure becomes simple, and manufacturing cost is low.

2. Description of the Related Art

In general, the interdental toothbrush has small brush-shaped bristles for cleaning spaces between the teeth mounted on the end of the handle. They are orally hygiene instruments used to clean the oral cavity by washing interdental spaces using putting in and pulling out motions of the brush in the interdental space gaps. Use of the interdental toothbrush facilitates removal of food-residue and plaque of hard-to-reach areas of usual toothbrushes, sterilization after dental treatment such as scaling, prevention of plaque after smoking, and cleaning of orthodontic instruments such as braces to maintain oral hygiene.

However, looking at the actual state of use of the current interdental brush, there are problems that the cleaning is conducted only using the brush and thus gums become stimulated, bleeding occurs frequently and the ability to remove food-residue and plaque becomes insufficient. Further, if interdental brushes are continuously used, there is an unpleasant smell from the brush due to a bad cleanliness, particularly, the growth of bacteria.

In an attempt to solve the above-mentioned problems, as shown in FIG. 1, there has been developed a toothbrush in which a lid 120 containing a cleaning solution 140 is coupled inside the toothbrush 110 coupled with bristles 130, and each time the user uses it, the toothbrush 110 is immersed in the cleaning solution so that the toothbrush 110 is soaked with the cleaning solution 130. However, this method has disadvantages in that the cleaning solution 140 is stored in the lid 120 of the toothbrush 110 and thus the cleaning solution can be discharged outside if the lid 120 is open due to the user's carelessness. Also, care should be taken for preventing loss of the cleaning solution stored in the lid 120 when using the toothbrush 110. Further, it is troublesome to repeat the motions of putting in and pulling out the toothbrush 110 in the lid 120 every time the user tries to soak the toothbrush 110 in the cleaning solution.

To solve the above problems, Korean Patent No. 10-0468075 titled "An interdental toothbrush provided with a cleaning solution" has been suggested. The interdental toothbrush disclosed in this patent comprises, as shown in FIG. 2, a case 40 having both ends open, a storage tank 30 installed in the case 40, on one side of which is formed a discharge hole 32, and the other side of which is open, a pleated tube 70 coupled to the open outer circumferential face of the storage tank 30 and to a check valve 80 joined to an end thereof a spring 55 installed on the outer circumferential face of the discharge hole 32, a coupling socket 50 installed on the outer circumferential face attic discharge hole 32 and having a screw part on the outer circumferential face thereof, a nozzle 60 screw-coupled to the discharge hole 32, an end portion of which is split into upper and lower parts, and having a cone-shaped discharge hole inside and a slanted bump 62 on an outer circumferential face thereof, a fixing ring 65 coupled to the split outer circumferential face of the nozzle 60 and contacted with a side surface of the coupling socket 50, and a nozzle cap 90 engaged in the screw portion formed on the coupling socket 50 and having a brush 95 assembled on the front surface thereof and a couple of injection holes 92 formed therein. This interdental toothbrush is effective in eliminating the inconvenience of handling cleaning solution of the prior art, however, the structure is complicated and the manufacturing cost is high, so it is not practical. Further, when the cleaning solution is all used up, the storage tank 30 should be replenished with a new cleaning solution, however, it is impossible to replenish the cleaning solution in the storage tank 30, which makes it impossible to continuously use the interdental toothbrush purchased at a high price.

SUMMARY

It is an object of the present invention to solve the above-described problems encountered with the prior arts and to provide a portable interdental toothbrush in which a cleaning solution containing fluoride is received in a sealed state and thus it is convenient to carry the toothbrush and ensure activity; the cleaning solution can be discharged during use by cutting an assembly tip of a cleaning solution tube storing the cleaning solution stored in a sealed state; the assembly groove for the cut assembly tip of the cleaning solution tube to be assembled is formed on the bottom surface, which enables the cleaning solution to easily supply to a brush of the brush body and provides simple structure, low manufacturing cost, and convenience in use.

Another object of the present invention is to solve the above-described problems and to provide a portable interdental toothbrush capable of replenishing the cleaning solution containing fluoride after use, thereby allowing long term use and convenience in use.

The above objects of the present invention is achieved by a portable interdental toothbrush according to the present invention comprising: a cleaning solution tube in which a cleaning solution containing fluoride is received in a sealed state to carry it conveniently, and a sealed assembly tip is formed to be cut out for use; and a brush body to which a brush is fixed, an inflow hole is formed on the edge of the brush, and an assembly groove that the assembly tip of the cleaning solution tube is assembled is formed on a bottom surface, wherein, during use, the sealed assembly tip of the cleaning solution tube is cut, the cut assembly tip is inserted in the assembly groove on the bottom surface of the brush body, the cleaning solution stored in the cleaning solution tube is discharged through the inflow hole of the brush body to wet the brush, thereby the cleaning solution is supplied.

The above objects of the present invention is achieved by a portable interdental toothbrush according to the present invention comprising: a cleaning solution tube filled of a cleaning solution containing fluoride to enable a filling, thus allowing a long-term use, which tube is operated so as to discharge a small amount of the filled cleaning solution upon pressing a push button, and an assembly tip is formed on one end thereof; and a brush body to which a brush is fixed, an inflow hole is formed on the edge of the brush, and an assembly groove to which the assembly tip of the cleaning solution tube is assembled is formed on a bottom surface, wherein, the assembly tip is inserted in the assembly groove on the bottom surface of the brush body, the cleaning solution stored in the cleaning solution tube is discharged through the inflow hole of the brush body to wet the brush, thereby the cleaning solution is supplied.

A portable interdental toothbrush according to the present invention can be carried conveniently since a cleaning solution tube stays in a sealed state when carried without using it, which provides convenience in use, simple structure, easy manufacture, and low production cost, thereby allowing any user to use it, which promotes the dental and oral health for citizens.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
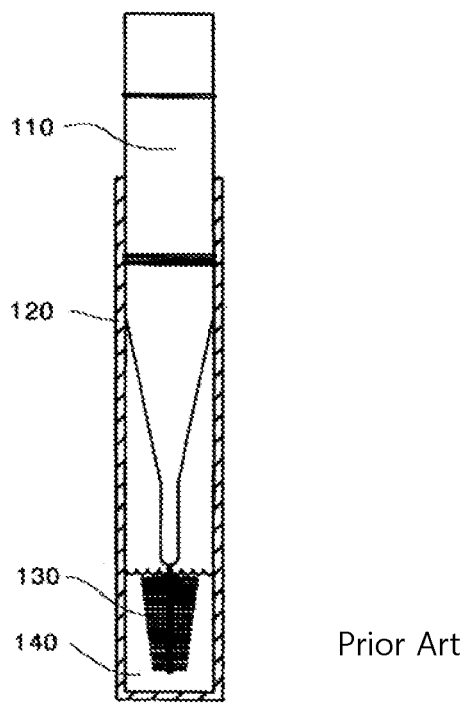
FIG. 1 is a longitudinal cross-sectional view of a conventional interdental toothbrush.
Figure 2:
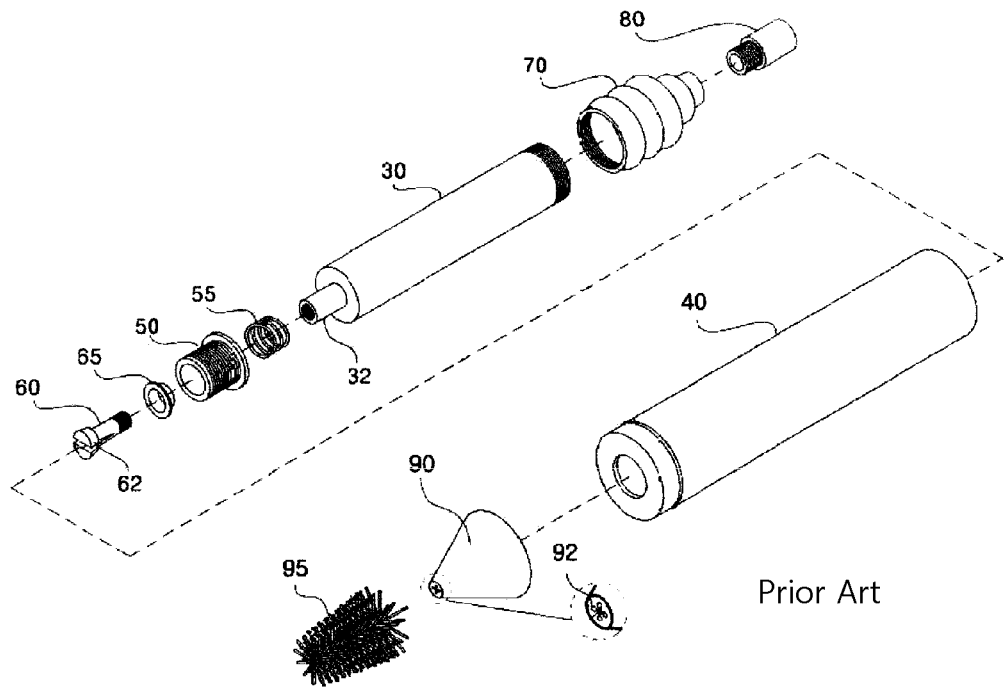
FIG. 2 is an exploded perspective view of another conventional interdental brush.

Hereinafter, the configuration and operation of preferred embodiments of the present invention will be described in detail with reference to the accompanying drawings. Here, in the case of assigning the reference numerals to the components of the drawings, it should be noted that, with respect to the same components, the same reference numerals are used even in different drawings.

Figure 3:
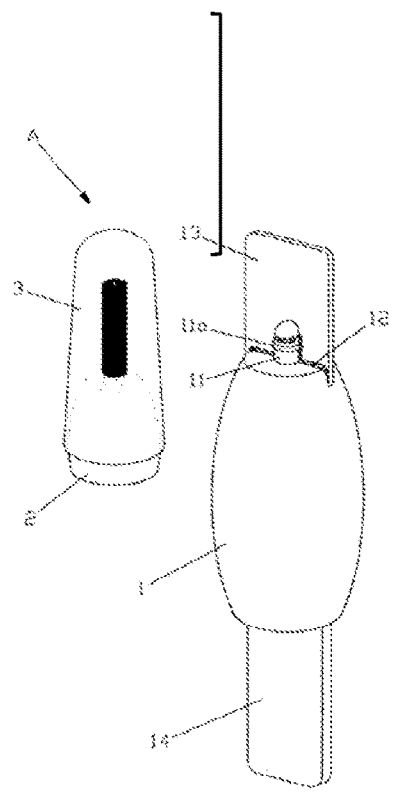
FIGS. 3 and 4 are perspective views of a portable interdental toothbrush in accordance with the first embodiment of the present invention during carrying and during use, respectively.
Figure 4:
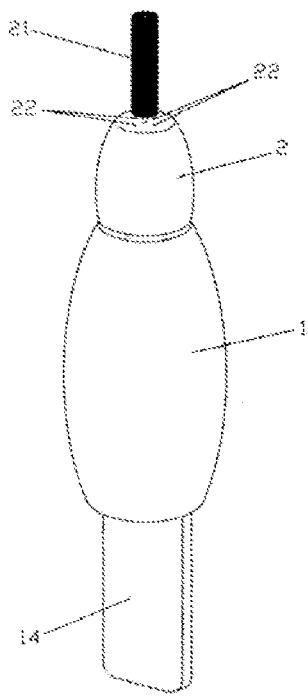
Figure 5:
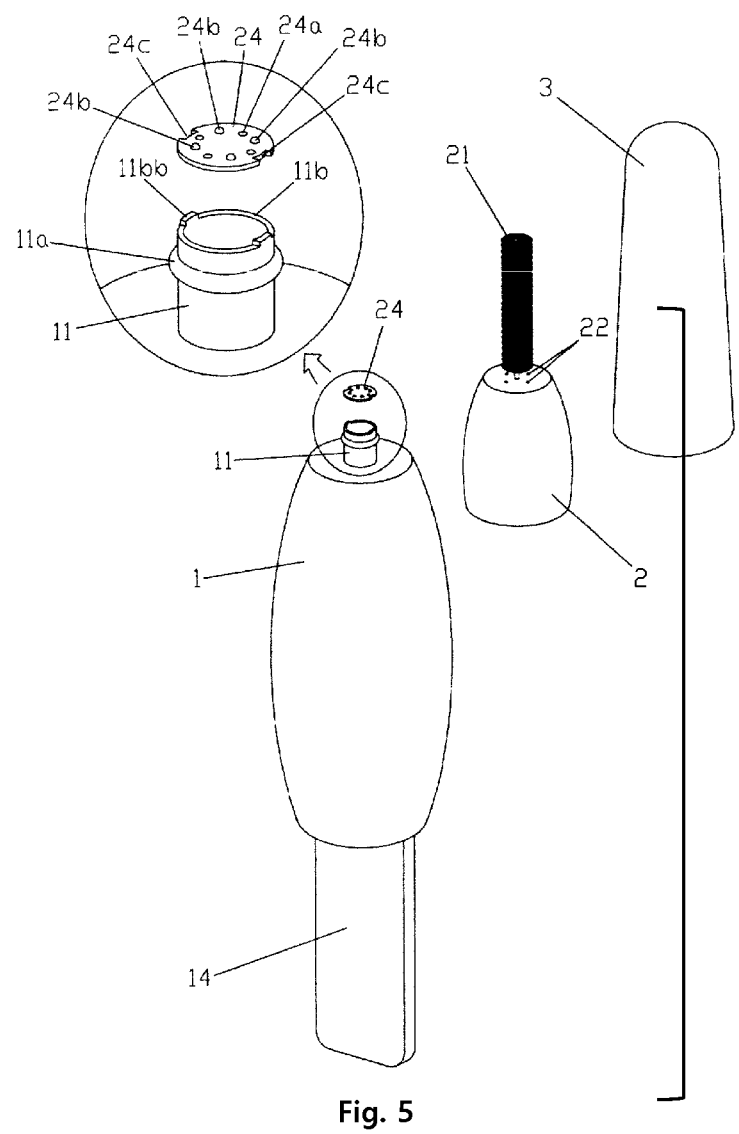
FIG. 5 is an exploded perspective view of a portable interdental toothbrush in accordance with the first embodiment of the present invention.
Figure 6:
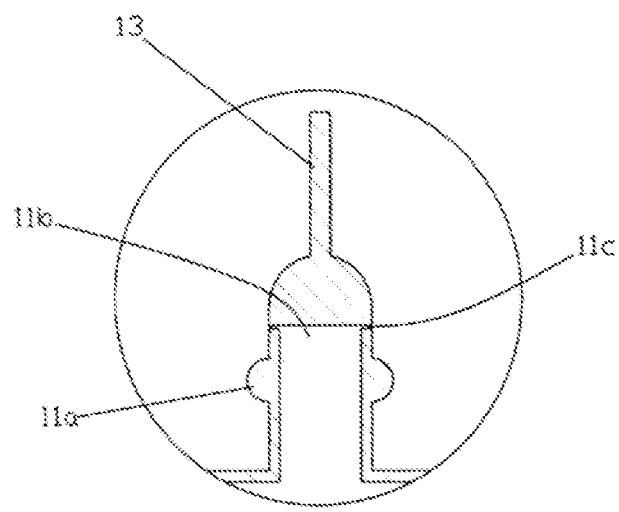
FIGS. 6 and 7 are longitudinal cross-sectional views of an assembly tip of a cleaning solution tube when it is carried and when it is assembled, respectively.
Figure 7:
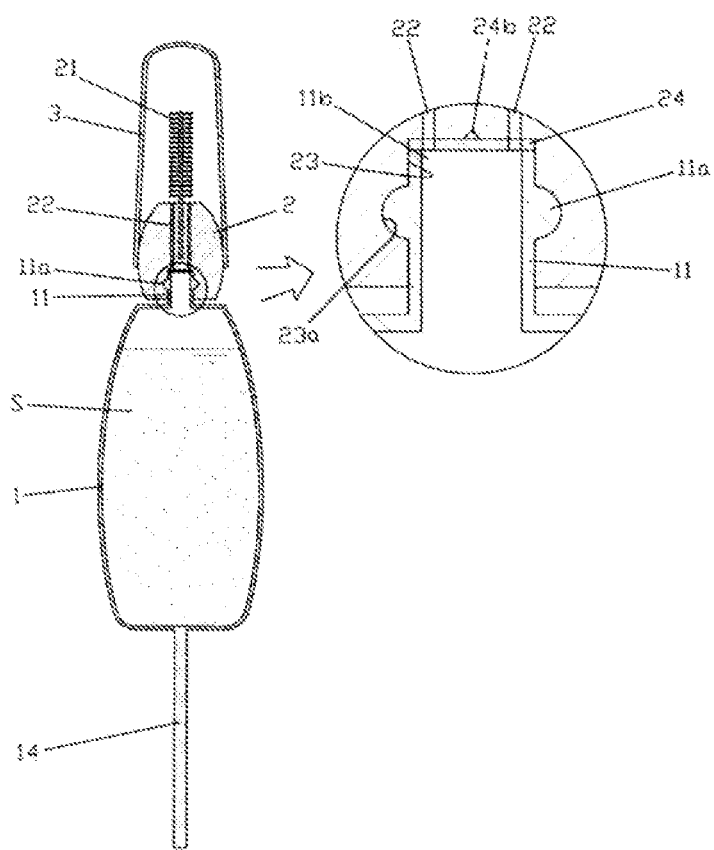

As shown in FIGS. 3 and 5, a portable interdental toothbrush A according to the first embodiment of the present invention comprises: a cleaning solution tube 1 in which a cleaning solution S containing fluoride is received in a sealed state and thus it is convenient to carry the toothbrush, and which tube is formed to enable the sealed assembly tip 11 to cut during use; and a brush body 2 to which a brush 21 is fixed, an inflow holes 22 are formed on the edge of the brush 21, and an assembly groove 23 that the assembly tip 11 of the cleaning solution tube 1 is assembled is formed on a bottom surface.

As shown in FIG. 3, the cleaning solution tube 1 is made of a transparent vinyl for easy manufacture. An assembly tip 11 is configured such that an assembly protrusion 11a is formed in the middle of the assembly tip 11, and a cutting groove 12 is formed for easy cutting around the assembly tip 11, thereby when pulling a protruded plate 13 of the upper part, the cutting groove 12 is cut and then an assembly portion 11c which is weakly coupled to an upper surface 11b of the assembly tip 11 is torn and the upper surface 11b is opened. Protrusions 11bb having a concavo-convex shape are formed on the cut upper surface 11b and are engaged with a side surface of an opening/closing plate 24 inserted into the brush body 2 to be described later, to prevent the rotation of the opening and shutting plate 24. An extended plate portion 14 which can be used as a grip is formed under the cleaning solution tube 1, thereby allowing insertion of an advertisement or other necessary contents. In this embodiment, the cleaning solution tube 1 is disposable to allow hygienic and convenient use.

Another embodiment of the cleaning solution tube 1 is a structure which does not need the opening opening and shutting plate 24, and the upper surface 11b of the assembly tip 11 is covered with a thin vinyl in a state where the cleaning solution S is filled, a perforating portion is marked at a location on the vinyl communicating with the inflow holes 22 of the brush body 2, thereby allowing a user to perforate the perforating portion and insert into the assembly groove 23 of the brush body 2 to use. While it is not used, the brush body 2 may be rotated slightly to close the inflow holes 22.

The brush body 2 utilizes an elastic silicon material. The brush 21 is fixed to the middle of an upper part, and four inflow holes 22 for communicating with the assembly groove 23 and flowing the cleaning solution S are formed on the edge of the brush 21. An assembly groove 23 is formed in the bottom surface of the brush body 2, and a ring shape assembly groove 23a is formed in the middle of the assembly groove 23 so that the assembly protrusion 11a is inserted and fixed. The opening and closing plate 24 is closely adhered to the bottom surface of the assembly groove 23 to perform opening and shutting operations of the inflow holes 22.

Grooves 24c for engaging with protrusions of the upper surface 11b are formed on the side of the opening and shutting plate 24 to fix the opening and shutting plate 24 without rotation. Four communicating holes 24a for communicating with the inflow holes 22 and press-fit protrusions 24b protruded between the communicating holes 24a are formed on the opening and shutting plate 24 such that the press-fit protrusions 24b close the bottom surface of the inflow holes 22 rotating together when the brush body 2 rotates to prevent the cleaning solution S from discharging.

The reference numeral 3 which is not described is a cover 3 for protecting the brush 21.

In this embodiment, the brush body 2 is made of a silicon material to enable a repetitive use. The operational effect of the portable interdental toothbrush A according to the present invention having the above configuration will be described in detail below.

When it is not used, but carried, the cleaning solution tube 1 and the brush body 2 are stored and carried in a separately separated state. When the protruded plate 13 of the cleaning solution tube 1 is pulled if the use is required, the cutting groove 12 formed along the outline of the assembly tip 11 is cut and concurrently the outline surface of the assembly tip 11 is cut, and further the upper surface 11b of the assembly tip 11 is torn, thereby the cleaning solution S is opened in a usable state.

In the state as described above, if the open assembly tip 11 of the cleaning solution tube 1 is inserted in the assembly groove 23 of the lower part of the brush body 2, this forces the assembly protrusion 11a of the assembly tip 11 to be mounted and inserted in a contracted state, and then again assembled in an expanded state while inserted in the ring shape assembly groove 23a formed in the middle of the assembly groove 23, thereby the assembly of the cleaning solution tube 1 and the brush body 2 is completed. In a state where the assembly of the cleaning solution tube 1 and the brush body 2 is completed, if the brush body 2 is inclined downward, the cleaning solution S stored in the cleaning solution tube 1 flows downward through the inflow holes 22 to wet the brush 21, thereby the cleaning solution S is wetted on the brush, which enables the portable interdental toothbrush A to use. By doing so, it is possible to easily use the portable interdental toothbrush. After use, if the brush body 2 is rotated slightly, the inflow holes 22 are closed to prevent the cleaning solution S from discharging, which allows the storage of the portable interdental toothbrush.

Figure 8:
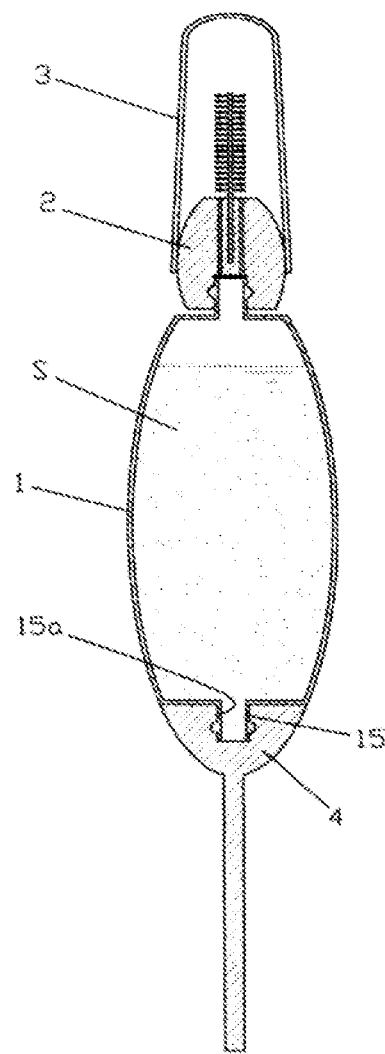
FIG. 8 is a longitudinal cross-sectional view of a portable interdental toothbrush in accordance with the second embodiment of the present invention.

FIG. 8 is a schematic longitudinal cross-sectional view of a portable interdental toothbrush in accordance with the second embodiment of the present invention. While the cleaning solution tube 1 is described as disposable in the first embodiment, a repeatedly usable structure of the portable interdental toothbrush A is suggested in the manner in which a lower assembly tip 15 having an injection hole 15a is formed in a lower part of the cleaning solution tube 1, and a sealing cover 4 made of a silicon material and having an upper assembly groove portion 41 formed in an upper part is formed to be inserted into and sealed with the lower assembly tip 15 such that, when the cleaning solution S inserted in the cleaning solution tube 1 is used up, the cleaning solution S can be replenished after taking off the sealing cover 4 and the sealing cover 4 is inserted and fixed again.

Figure 9:
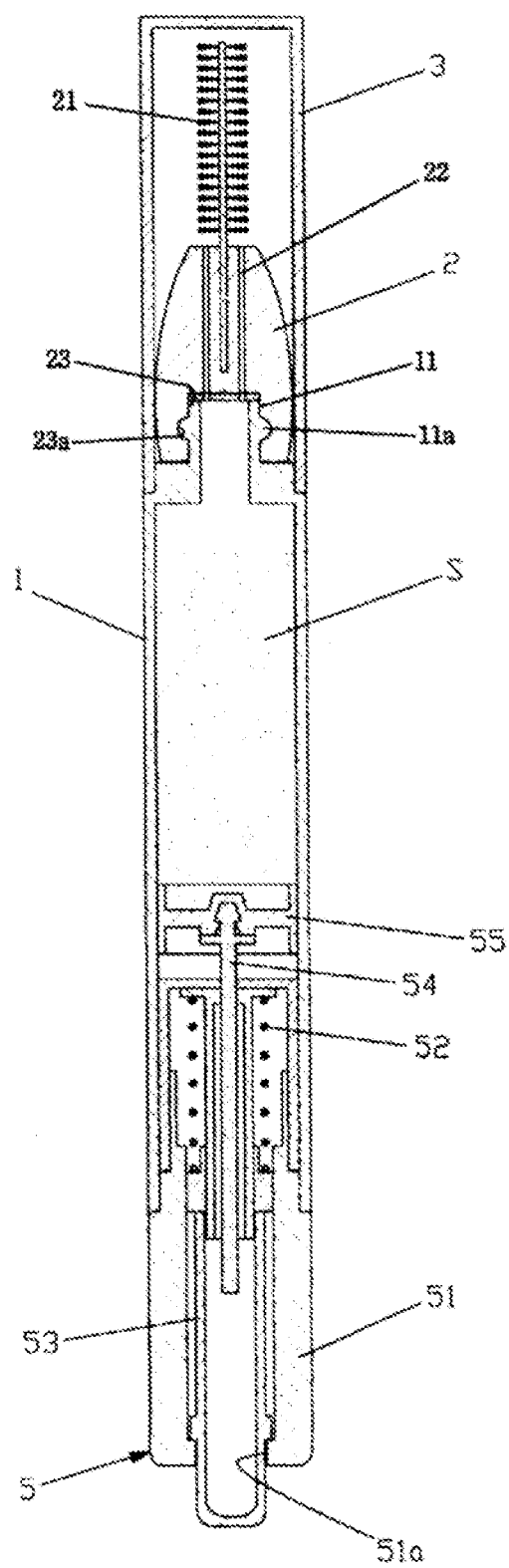
FIG. 9 is a longitudinal cross-sectional view of a portable interdental toothbrush in accordance with the third embodiment of the present invention.

FIG. 9 is a schematic longitudinal cross-sectional view of a portable interdental toothbrush A in accordance with the third embodiment of the present invention, and this also has a structure capable infusing by repeatedly injecting the cleaning solution S. The brush body 2 has the same structure as in the above-mentioned embodiment and thus the detailed description thereof is omitted. The cleaning solution tube 1 has an improved structure to use it conveniently.

The cleaning solution tube 1 has a pipe type of a syringe shape in which the cleaning solution S is filled, one end of which is formed of an assembly tip 11 which can he inserted into the assembly groove 23 of the brush body 2, and the other end is open. A pressing piston unit 5 for pressing the filled cleaning solution S to the assembly tip 15 is formed on the other open end. The pressing piston unit 5 includes a casing 51 coupled to the other end of the cleaning solution tube 1; a push button 53 which is placed inside the casing 51 and one end of which is protruded through an assembly hole 51a of the one end of the casing 51 and supported elastically by a spring 52; and a pressing shaft 54 which is fixed to an inside end portion of the push button 53 and interlocked with an operation of the push button 53 and in which a pressing plate 55 for pressing the cleaning solution S is attached to one end thereof.

Accordingly, upon pressing the protruded end of the push button 53, the pressing plate 55 moves to press the filled cleaning solution S, the pressed cleaning solution S is discharged through the assembly tip 11 and supplied to the brush 21 through the inflow holes 22 of the brush body 2. When the cleaning solution S is used up, the cleaning solution S is replenished through the assembly tip 11 after taking off the brush body 2, which allow repeated use.

Figure 10:
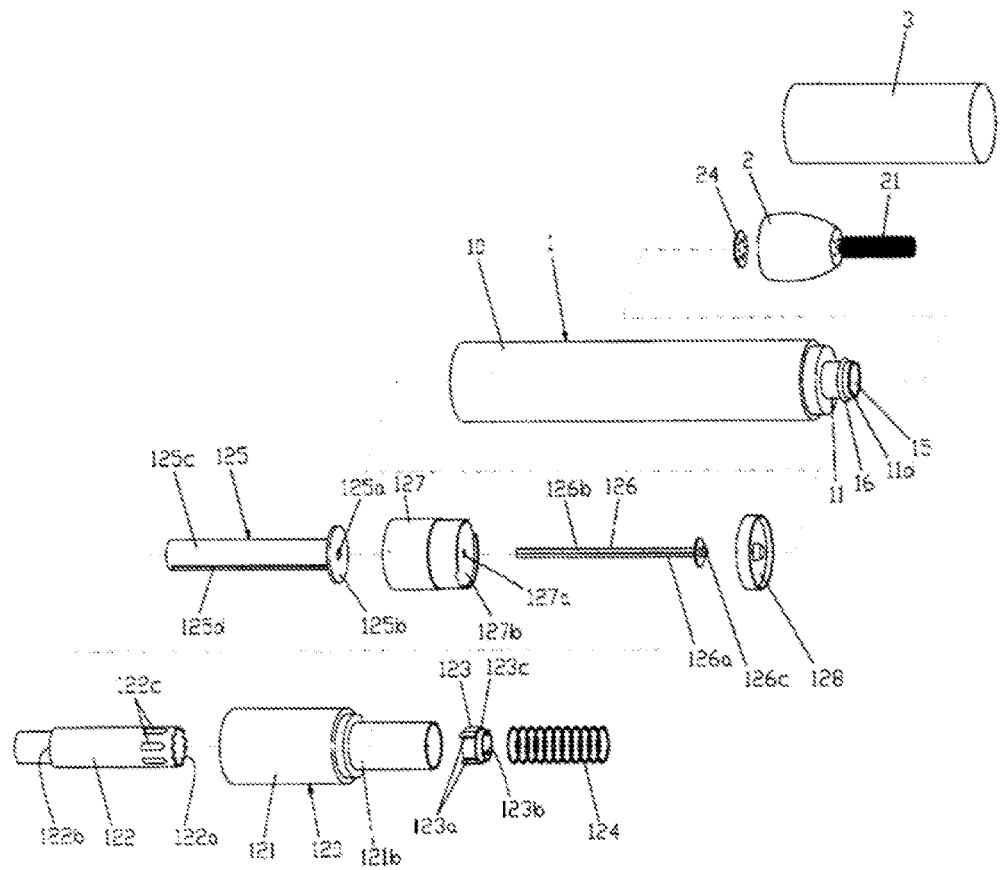
FIG. 10 is an exploded perspective view of a portable interdental toothbrush in accordance with the fourth embodiment of the present invention.
Figure 11:
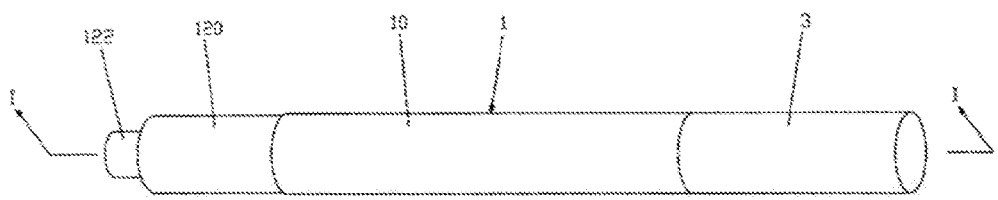
FIG. 11 is a perspective view of a portable interdental toothbrush in accordance with the fourth embodiment of the present invention.
Figure 12:
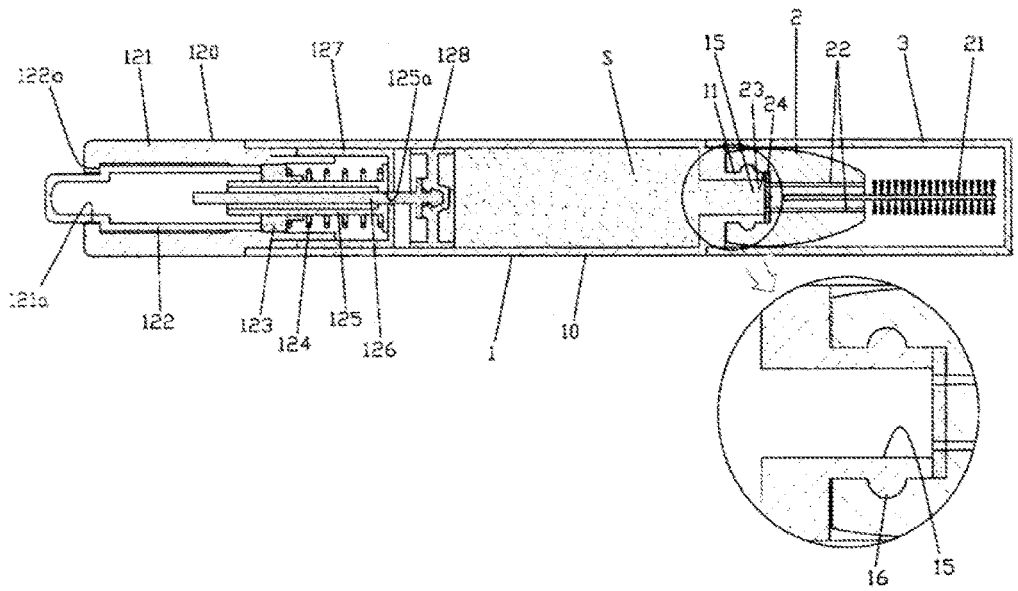
FIG. 12 is a cross-sectional view along I-I line of FIG. 11.
Figure 13:
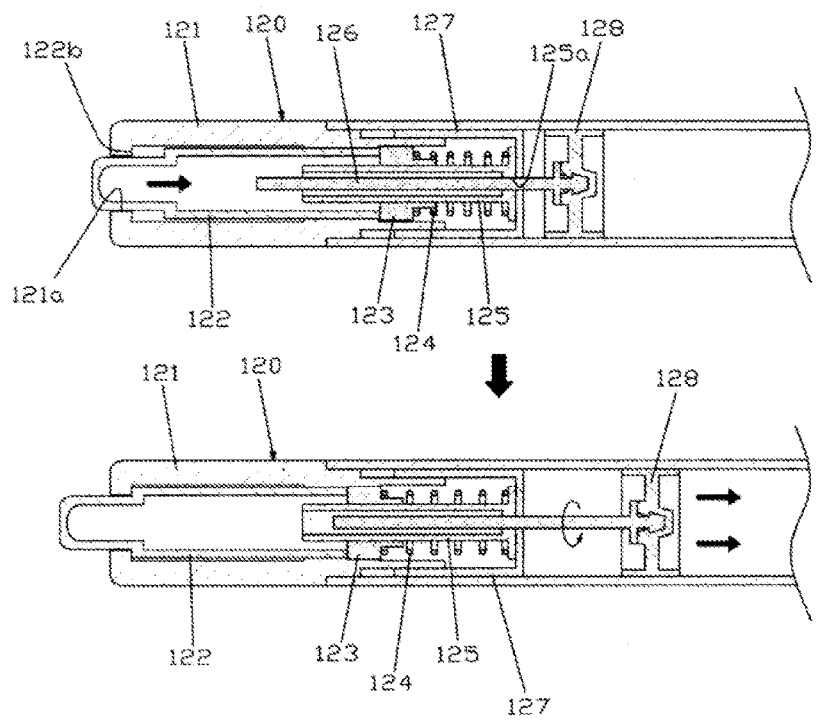
FIG. 13 is a longitudinal cross-sectional view showing an operation state of a button unit of a portable interdental toothbrush in accordance with the fourth embodiment of the present invention.
Figure 14:
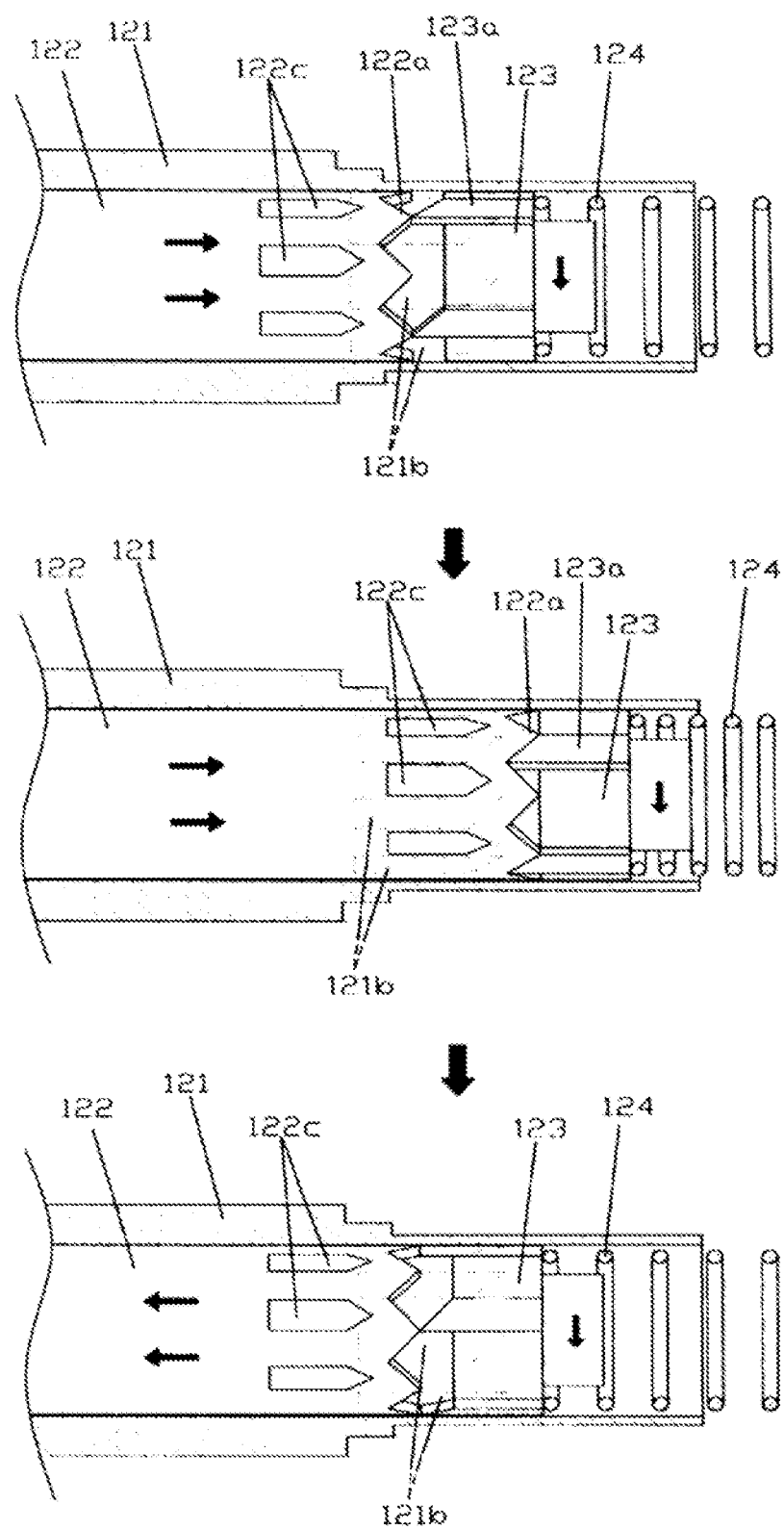
FIG. 14 is an operation view illustrating an operation of a portable interdental toothbrush in accordance with an embodiment of the present invention.

As shown in FIGS. 10-12, a portable interdental toothbrush A according to the fourth embodiment of the present invention comprises: a cleaning solution tube 1 in which a cleaning solution S containing fluoride is filled in the inside and, upon pressing a push button for use, the cleaning solution S is discharged through a discharge hole 15 of an assembly tip 11 formed on one end, and a brush body 2 to which a brush 21 is fixed, inflow holes 22 are formed on the edge of the brush 21, and an assembly groove 23 to which the assembly tip 11 of the cleaning solution tube 1 is assembled is formed on a bottom surface.

As shown in FIG. 10, the cleaning solution tube 1 is made of transparent synthetic resins; however, it may also be made of semi-transparent or opaque synthetic resins.

The cleaning solution tube 1 includes a tubular shape tube body 10 which is filled with the cleaning solution S therein, one end of which is formed of the open assembly tip 11, and the other end is open; and a cleaning solution-pressing unit 120 assembled with the other open end for pressing the cleaning solution S in the direction of the assembly tip 11. In the assembly tip 11 formed on one end of the tube body 10, a discharge hole 15 is formed in a center, an assembly protrusion 16 is formed in the middle of outer surface, protrusions 11d having a concavo-convex shape are formed on an upper surface of the assembly tip 11, which engage with the sides of the opening and shutting plate 24 inserted to the brush body 2, which will be described later, to prevent the opening and shutting plate 24 from rotating.

The other end of the tube body 10 is open and the cleaning solution pressing unit 120 is fixed thereto.

The cleaning solution-pressing unit 120 includes: a casing 121 coupled to the other open end of the tube body 10; a push button 122 in which one end thereof is located inside the casing 121 and the other end is protruded through the assembly hole 121a of one side end portion of the casing 121; a rotating member 123 for contacting the one end of the push button 122 located inside the casing 121 and interlocked with an operation of the push button 122; a spring 124 for supporting the rotating member 123; a rotating rod 125 which is inserted and fixed inside the rotating member 123 and rotating together with the rotation of the rotating member 123, in which a pressing shaft insertion hole 125a for a pressing shaft 126 to be inserted and fixed is formed; an inner casing 127, one end of which is closed and a shaft fixing hole 127a for a pressing shaft 126 to be inserted and fixed thereto is formed, and the other end of which is open and one end of the rotating rod 125 is placed adjacent thereto; a pressing shall 126 which is inserted into the shaft fixing hole 127a of the inner casing 127 to be inserted into the pressing shaft insertion hole 125a of the rotating rod 125 and in which a pressing plate 128 is formed on one end; and a pressing plate 128 fixed to one end of the pressing shaft 126 and placed inside the tube body 10 to press the cleaning solution S in the direction of the assembly tip 11.

One end of the casing 121 is fixed to the open end of the tube body 10, and an assembly hole 121a is perforated on the other end. Inside of the lower side end portion of the casing where the width is narrow, rotation guide protrusions 121b protruded inwardly having an inclined surface formed on one end thereof are formed with regular intervals.

The push button 122 has a tubular shape having a hollow, one end of which is protruded outward through the assembly hole 121a of the casing 121, a sawtooth contact portion 122a having an overlapping mountain shape is formed on the other end, and an engaging protrusion 122b is formed in the middle. Protrusion guide portions 122c protruded outward with regular intervals and pointed in the direction of the sawtooth contact portion 122a are formed on an outside surface of the end on which the sawtooth contact portion 122a of the push button 122 is formed.

In the rotating member 123, four half-sawteeth 123a which contact and rotate with the sawtooth contact portion 122a of the push button 122 are formed on the outside surface with regular intervals, four fixing grooves 123b for fixing the assembly protrusions 125d of the extended pipe portion 125c of the rotating rod 125 are formed inside with regular intervals, and a spring contact surface 123c is formed on a surface adjacent to the spring 124.

In the rotating rod 125, a spring contact plate 125b for contacting the spring 124 is formed on one end, a pressing shaft insertion hole 125a is formed as a screw groove on a center of the spring contact plate 125b, the extended pipe portion 125c extended lengthily is formed in the rear of the spring contact plate 125b, an assembly protrusion 125d is formed outside the extended pipe portion 125c, and the assembly protrusion 125d is inserted into the fixing groove 123b of the rotating member 123, whereby the rotating member 123 and the rotating rod 125 rotationally operate together.

A thread 126b is formed outside of an extended rod 126a extended lengthily for screw-coupling to the pressing shall insertion hole 125a of the rotating rod 125, which makes one end of the pressing shaft 126 to screw-couple to the rotating rod 125, and a protruded assembly portion 126c for attaching and detaching the pressing plate 128 is formed on the other end of the pressing shaft 126.

The inner casing 127 is rotationably inserted into an inner surface of the tube body 10 and supports the rotating rod 125 to prevent from separating forwardly. On a contact surface adjacent to the rotating rod 125, a shaft fixing hole 127a having an upper and lower cut circular shape which is the same as the cross section of the extended rod 126a of the pressing shaft 126 on the center of the contact surface 127b is formed and the inner casing 127 rotates simultaneously when the pressing shaft 126 rotates.

The pressing plate 128 adheres closely to the inside of the tube body 10 to press the cleaning solution S in the direction of the brush body 2.

The brush body 2 is made of an elastic silicon material. The brush 21 is fixed on the center of the upper part, four inflow holes 22 for communicating an assembly groove 23 of the lower part and flowing the cleaning solution S are formed on the periphery of the brush 21. The assembly groove 23 is formed on a bottom surface, and a ring shape assembly groove 23a for the assembly protrusion 16 formed in the middle of the assembly tip 11 to be fixed when the assembly tip 11 formed on one end of the tube body 10 is inserted is formed in the middle of the assembly groove 23.

An opening and shutting plate 24 is closely adhered to the bottom surface of the assembly groove 23 to perform opening and shutting operations of the inflow holes 22. Grooves (24c) for engaging with protrusions 11d of the upper surface are formed on a side surface of the opening and shutting plate 24 to fix the opening and shutting plate 24 without rotation. On the opening and shutting plate 24 are formed four communicating holes 24a for communicating with the inflow holes 22 and press-fit protrusions 24b protruded between the communicating holes 24a, whereby the press-fit protrusions 24b close the bottom surfaces of the inflow holes 22 which are rotated together during rotation of the brush body 2 to prevent the cleaning solution S from discharging.

The operational effect of the portable interdental toothbrush A according to the present invention having the above configuration will be described below in detail.

In a state where the cleaning solution S is filled, the push button 122 is pressed to use the portable interdental toothbrush A. Then, the push button 122 descends, the sawtooth contact portion 122a of the lower part descends to press the half-sawteeth 123a of the rotating member 123 which is point-contacted. The half-sawteeth 123a rotate in the direction of the arrow to plane-contact with the descended sawtooth contact portion 122a (See FIG. 12). When the rotating member 123 rotates, the rotating rod 125 connected integrally thereto rotates as a matter of course. Then, the pressing shaft 126 screw-coupled to the pressing shall insertion hole 125a of the rotating rod 125 to move the pressing plate 128 fixed to one end of the pressing shaft 126 forward in the direction of the cleaning solution S. The pressed cleaning solution S is supplied to the brush 21 through the inflow holes 22 of the brush body 2.

If the pressure on the push button 122 is released in the state that the half-sawteeth 123a and the sawtooth contact portion 122a are surface-contacted, the push button 122 is expelled by the spring 124 to one side and moved upward with the guidance of the rotation guide protrusions 121b formed on the inner snake of the casing 121. By the repetition of the above-described operation, the push button moves upward and downward to discharge the cleaning solution S to the brush body 2.

If the cleaning solution S is used up, the brush body 2 is separated from the cleaning solution tube 1 easily by pulling out the brush body 2. After the cleaning solution S is replenished through the discharge hole 11a of the assembly tip 11 of the cleaning solution tube 1, it may be continuously used.

It is possible to manufacture the same products as the portable interdental toothbrush in accordance with the present invention repeatedly in the manufacturing field of the interdental toothbrush. Accordingly, the present invention possesses industrial applicability.

Although the specific embodiments of the present invention have been disclosed for illustrative purposes, those skilled in the art will appreciate that various modifications, additions and substitutions may be made to the invention without departing from the scope and spirit of the invention as disclosed in the accompanying claims.

What is claimed is:
1. A portable interdental toothbrush comprising:
a cleaning solution tube filled with a cleaning solution and formed such that a push button is pressed during use and then the cleaning solution is discharged through a discharge hole of an assembly tip which is formed on one end; and a brush body to which a brush is fixed, an inflow hole is formed on the edge of the brush, and an assembly groove to which the assembly tip of the cleaning solution tube is assembled is formed on a bottom surface of the brush body, wherein, the cleaning solution tube includes a tubular shape tube body which is filled with the cleaning solution therein, one end of which is formed of the open assembly tip and the other end is opened, and a cleaning solution pressing unit assembled with the other open end of the tube body for pressing the cleaning solution in the direction of the assembly tip, the assembly tip formed on one end of the tube body is configured such that the discharge hole is formed in a middle of the assembly tip, and an assembly protrusion is formed in a middle of an outside portion of the assembly tip, and the cleaning solution pressing unit includes a casing coupled to the other open end of the tube body, the push button in which one end thereof is located inside the casing and the other end is protruded through an assembly hole of one side end portion of the casing, a rotating member for contacting one end of the push button located inside the casing and rotates with an operation of the push button, a spring for supporting the rotating member, a rotating rod which is inserted and fixed inside the rotating member and rotating together with a rotation of the rotating member, in which a pressing shaft insertion hole for a pressing shaft to be inserted and fixed is formed, an inner casing, one end of which is closed and a shaft fixing hole for the pressing shaft to be inserted and fixed thereto is formed, and the other end of which is open and one end of the rotating rod is placed adjacent thereto, the pressing shaft which is inserted into the shaft fixing hole of the inner casing to be inserted into the pressing shaft insertion hole of the rotating rod and in which a pressing plate is formed on one end, and the pressing plate fixed to one end of the pressing shaft and placed inside the tube body to press the cleaning solution in a direction of the assembly tip.

2. The portable interdental toothbrush of claim 1 wherein the brush body is configured such that the brush is fixed to a middle of an upper part, a plurality of inflow holes which penetrate the assembly groove and through which the cleaning solution flows are formed on the edge of the brush, the assembly groove is formed on the bottom surface of the brush body and a ring shape assembly groove is formed in the middle of the assembly groove so that the assembly protrusion is inserted and fixed.

3. The portable interdental toothbrush of claim 2 wherein an opening and shutting plate is adhered closely to a bottom surface of the assembly groove, a groove for engaging with a protrusion of an upper surface is formed in the opening and shutting plate, and a communicating hole for communicating with the inflow hole is formed in the opening and shutting plate.

* * * * *